United States Patent [19]

Nohara et al.

[11] 3,984,441
[45] Oct. 5, 1976

[54] CHROMONEALDEHYDE COMPOUNDS AND PROCESS FOR THE PRODUCTION THEREOF

[75] Inventors: Akira Nohara, Kyoto; Tomonobu Umetani, Osaka; Yoshibumi Miyata, Osaka; Yasushi Sanno, Osaka, all of Japan

[73] Assignee: Takeda Chemical Industries, Ltd., Osaka, Japan

[22] Filed: Nov. 2, 1972

[21] Appl. No.: 303,046

Related U.S. Application Data

[63] Continuation-in-part of Ser. No. 155,216, June 21, 1971, abandoned.

[30] Foreign Application Priority Data

Nov. 4, 1971 Japan.............................. 46-87880
Dec. 27, 1971 Japan.............................. 47-1698

[52] U.S. Cl.......................... 260/345.2; 260/345.5; 424/283
[51] Int. Cl.².................................... C07D 311/30
[58] Field of Search...................... 260/345.2, 345.5

[56] References Cited
FOREIGN PATENTS OR APPLICATIONS 769,146  11/1971  Belgium
777,544  4/1972  Belgium

OTHER PUBLICATIONS

Eiden et al., *Arch der Pharm*, vol. 300, pp. 806–810 (1967).

Fieser et al., "Advanced Organic Chemistry", p. 416, Reinhold Pub. Co. New York, (1961).

*Primary Examiner*—John M. Ford
*Attorney, Agent, or Firm*—Burgess Ryan and Wayne

[57] ABSTRACT

There are provided compounds of the general formula

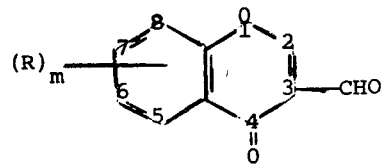

wherein R is a hydroxy, alkyl, acyloxy, halogen, nitro, substituted or unsubstituted amino, alkoxy, carboxy or a group derived from a carboxy group and $m$ is 0, 1 or 2 except where $m$ is 2, the two R groups are both hydroxy groups.

The present invention is also concerned with a process for preparing the chromonealdehyde compounds. The chromonealdehyde compounds are characterized by antiallergic properties and are therefore useful as prophylactic and therapeutic agents for allergic asthma, allergic dermatitis and other allergic diseases and also are valuable as intermediates for the synthesis of other pharmaceutical compounds having the chromone nucleus.

18 Claims, No Drawings

CHROMONEALDEHYDE COMPOUNDS AND PROCESS FOR THE PRODUCTION THEREOF

The present invention is a continuation-in-part of U.S. application Ser. No. 155,216 filed June 21, now abandoned.

The present invention relates to chromonealdehyde compounds of the formula

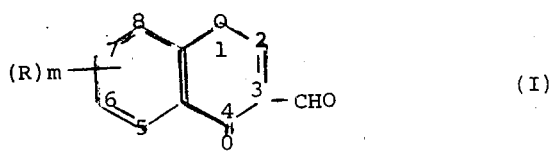

wherein R is a hydroxy, alkyl, acyloxy, halogen, nitro, substituted or unsubstituted amino, alkoxy, carboxy or a group derived from a carboxy group and $m$ is 0, 1 or 2 except where $m$ is 2, and the two R groups are both hydroxy groups.

The chromonealdehyde compounds of the present invention are useful as they possess antiallergic properties and are therefore not only useful as prophylactic and therapeutic agents for allergic asthma, allergic dermatitis and other allergic diseases but these compounds are also valuable as intermediates for the synthesis of other pharmaceuticals having the chromone nucleus. Thus, these compounds can be converted to the corresponding chromone-carboxylic acid compounds by subjecting the aforesaid aldehyde compound to oxidation.

The chromonealdehyde compounds of the present invention are prepared by reacting a compound of the formula

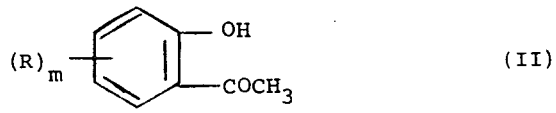

wherein R and $m$ are as defined above, with a compound of the formula

wherein $R_1$ and $R_2$ are the same or different and represent hydrogen, alkyl or an aryl group, and $R_1$ and $R_2$ when taken together with the adjacent nitrogen atom, may constitute a cyclic amino group in the presence of an acid halide.

In the formulae set out above, the alkyl groups designated by R, $R_1$ or $R_2$ include straight chain, branched or cyclic alkyl groups containing from 1 to 6 carbon atoms and illustratively, methyl, ethyl, propyl, isopropyl, butyl, isobutyl, t-butyl, pentyl, cyclopentyl, hexyl, cyclohexyl, and the like. Alkyl groups containing from 1 to 3 carbon atoms have been found to be most suitable. The halogen atom represented by R may be chlorine, bromine, iodine or fluorine.

When the amino group R is a substituted amino group, it may be a mono- or di-substituted amino group, the substituents being hydrocarbon residues, such as an alkylamino, arylamino or aralkylamino group, or an acylamino group, for instance. The alkylamino group thus designated by R may be an amino group substituted by a lower alkyl group of 1 to 3 carbon atoms, such as methylamino, ethylamino, propylamino, dimethylamino, diethylamino, dipropylamino, and the like. The arylamino group mentioned above may for example be phenylamino or diphenylamino; the aralkylamino group may for example be benzylamino or phenethylamino. The acylamino group R may be an amino group substituted by a lower alkylcarbonyl group of 1 to 3 carbon atoms or an arylcarbonyl group, such as acetyl, propionyl, butyryl or benzoyl. When R is an alkoxy group, it may be an alkoxy group wherein the alkyl moiety has 1 to 4 carbon atoms and illustratively methoxy, ethoxy, propoxy, butoxy, and the like. The acyloxy represented by R may be a lower alkylcarbonyloxy group of 1 to 3 carbon atoms or an arylcarbonyloxy group such as acetoxy, propionyloxy, butyryloxy, benzoyloxyl, and the like. The group derived from carboxyl which is also represented by R, is a group represented by the formula $-CONH_2$, $-CONR'R''$, or $-COOR'$ ($R'$ or $R''$ is an alkyl group such as methyl, ethyl or propyl or an aralkyl groups such as benzyl). When $m$ is equal to 1 or 2, these groups represented by R may be the same or different and occur in optional positions on the benzene ring.

The aryl group represented by $R_1$ or $R_2$ may for example be phenyl, tolyl or naphthyl. The cycloamino group formed by $R_1$ and $R_2$ when they are taken together with the adjacent nitrogen atom may for example be a 5 or 6-membered heterocyclic group containing from 1 to 2 nitrogen or oxygen atoms as heteroatoms and illustratively, piperazino, N-substituted piperazino, piperidino, morpholino, pyrrolidino, and the like.

As indicated above, the desired chromonenaldehyde compounds of the present invention are prepared by reacting a compound of the formula (II) with a compound of general formula (III) in the presence of an acid halide. While this reaction can be effected without the use of a solvent, it has been found that the reaction proceeds more smoothly by employing a suitable solvent or an excess of the compound (III) by employing a solvent as well as a reactant. The solvent used in the above reaction includes a hydrocarbon such as benzene or toluene, an organic acid such as formic acid, acetic acid or propionic acid, an ether such as ethyl ether, dioxane or tetrahydrofuran, or dimethylsulfoxide. While the present reaction proceeds at room temperature, it may also proceed at a low temperature (e.g. under cooling down to about −20°C) or by heating (e.g. at the boiling point of the solvent being used or at an elevated temperature up to about 150°C). In other words, the reaction temperature is largely optional. The reaction time is also largely optional and generally ranges from about 1 to about 24 hours. As regards the proportion of compound (III), generally good yields are expected when two moles or more of compound (III) is used for each mole of compound (II). Generally, the range of about 2 to about 10 moles is suitable.

The acid halides employed in the reaction are halides (fluoride, chloride, bromide or iodide) of a suitable inorganic or organic acid. By way of illustration, phosphorus oxychloride, phosphorus pentachloride, phosphorus pentabromide, phosphorus trichloride, tetrachloropyrophosphate, and the like, are suitable as halides of phosphoric or pyrophosphoric acid; thionyl chloride (SOCl$_2$), sulfuryl chloride (SO$_2$Cl$_2$), and the like, are illustrative of halides of sulfuric or sulfurous acid; and phosgene and thiophosgene are suitable as halides of carbonic acid. As halides or organic acids, there may be employed halides of aromatic acids such as benzoyl chloride, benzoyl bromide, and the like; halides of aliphatic acids such as acetyl chloride, acetyl bromide, and the like; and halides of sulfonic acid such as methanesulfonyl chloride, benzenesulfonyl chloride, p-toluenesulfonyl chloride, and the like. For practical purposes, about 2 to about 6 moles of such an acid halide is generally used for each mole of compound (II).

The desired compounds of the present invention represented by formula (I), which can be produced in the above manner, can be isolated and purified by conventional procedures such as for example, extraction, phasic transfer, chromatography and recrystallization.

The desired products of formula (I) are converted to the corresponding bisulfite-addition products upon being treated (e.g. heated) with a suitable sulfite (e.g. sodium hydrogen sulfite) in a suitable solvent (e.g. water). Compared with the end product (I), the above adduct is more readily soluble in water and can be more easily processed into various dosage forms such as injections and solutions.

When the desired product of general formula (I) or the bisulfite-addition products corresponding thereto is employed as a prophylactic or therapeutic agent for allergic diseases, it may be administered in such parenteral dosage forms as by injection, as an inhalant, ointments, and the like, or orally in the form of tablets, capsules, powders, solutions, and the like, usually at the daily dosage level for adults of about 1 to 500 mg.

The starting compounds of general formula (II) are prepared by, for example, the following methods.

ence of a catalyst (e.g. copper dust, potassium iodide, ferrous chloride, cuprous iodide or copper sulfate) at an elevated pressure; or c. by permitting a suitable alkylating agent (e.g, an alkyl halide such as methyl iodide or ethyl iodide or an dialkyl sulfate such as dimethyl sulfate or diethyl sulfate) or aralkylating agent (e.g. benzyl chloride or dibenzyl bromide) to act upon a compound (C) in an inert solvent (e.g. benzene) to alkylate or aralkylate the amino group or groups of the latter compound.

The following Examples are submitted as illustrating the invention but are not to be intended to be limiting. Where the word "part(s)" is used, this is based on weight unless otherwise indicated and the relationship between part(s) and "volume part(s)" corresponds to that between "gram(s)" and "milliliter(s)".

EXAMPLE 1

In 80 volume parts of diemthylformamide there is dissolved 25 parts of orthohydroxyacetophenone and while the solution is externally cooled to about −20°C with dry ice-acetone, 80 volume parts of tetrachloropyrophosphate is added in small installments. The mixture is stirred at room temperature for 13 hours. The reaction mixture is then poured into ice-water and the resulting crystals are recovered by filtration, washed with water and ethanol and finally recrystallized from acetone. There is obtained a 19.6 parts yield of 4-oxo-4H-1-benzopyran-3-carboxaldehyde, as colorless crystals, melting at 152°–153°C.

Analysis for C$_{18}$H$_{12}$O$_4$: Calcd. C, 73.97; H, 4.14 Found C, 73.88; H, 4.23

EXAMPLE 2

In 35 volume parts of dimethylformamide there is dissolved 8.8 parts of 2-hydroxy-4-acetoxyacetophenone and while the solution is externally cooled with

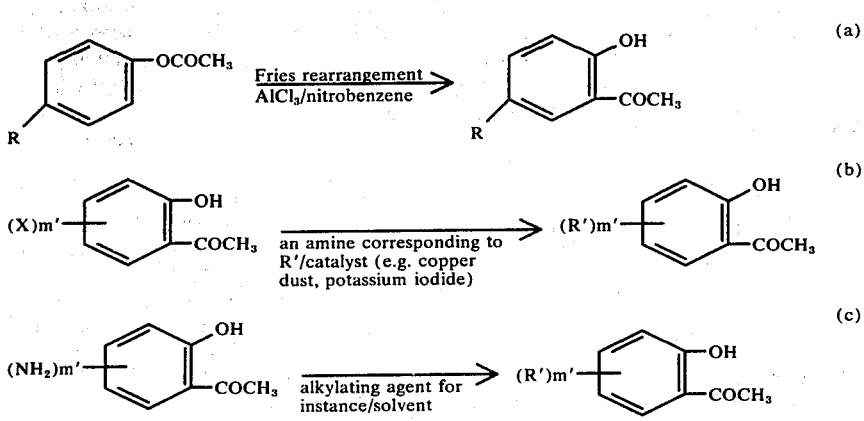

wherein X is a halogen atom (e.g. Cl, Br or I), R' represents R when the latter is an amino group substituted by the hydrocarbons as previously defined; m' is a whole number of 1 2; R is an previously defined.

Thus, the above compounds can be prepared by, for example:

a. causing the acetyl derivatives of a p-substituted phenol (A) to undergo a Fries rearrangement using aluminum chloride in suitable solvent (e.g. nitrobenzene);

b. heating a halogen derivative of acetophenone (B) and an amine corresponding to R$^1$ together in the presdry ice-acetone to about −20°C, 17 volume parts of phosphorus oxychloride is added dropwise. The temperature is gradually raised to room temperature and, then the reaction system is allowed to stand overnight. Next morning the reaction mixture is poured into ice-water and the resulting crystals are recovered by filtration and recrystallized from acetone. There is obtained an 8.7 parts yield of 7-acetoxy-4-oxo-4H-1-benzpyran-3-carboxaldehyde, as pale yellowish crystals, melting at 157° − 159°C.

Analysis for C$_{12}$H$_8$O$_5$: Calcd. C, 62.07; H, 3.47; Found C, 62.12; H, 3.43

The following compounds are synthesized by procedures similar to the procedure set forth in Example 2 supra,

| Starting materials | Product | Crystal form/Recrystallization solvent | m.p.(°C) | Example No. |
|---|---|---|---|---|
| 2-Hydroxy-4,6-diacetoxy-acetophenone + Dimethylformamide | 5,7-Diacetoxy-4-oxo-4H-1-benzopyran-3-carboxaldehyde | Colorless long needles/acetone | 162–163 (decomp.) | 3 |
| 2-Hydroxy-4,5-diacetoxy-acetophenone + Dimethylformamide | 6,7-Diacetoxy-4-oxo-4H-1-benzopyran-3-carboxaldehyde | Colorless scales/acetone | 140°–141° | 4 |
| 2-Hydroxy-6-acetoxy-acetophenone + Dimethylformamide | 5-Acetoxy-4-oxo-4H-1-benzophran-3-carboxaldehyde | Colorless needles/acetone | 174.5–176.5 | 5 |
| 2-Hydroxy-5-methyl-acetophenone + Dimethylformamide | 6-Methyl-4-oxo-4H-1-benzopyran-3-carboxaldehyde | White scales/acetone | 174/175 | 6 |
| 2-Hydroxy-5-chloro-acetophenone + Dimethylformamide | 6-Chloro-4-oxo-4H-1-benzopyran-3-carboxaldehyde | White scales/acetone | 166–168 | 7 |
| 2-Hydroxy-5-carboxy-acetophenone + Dimethylformamide | 6-Carboxy-4-oxo-4H-1-benzopyran-3-carboxaldehyde | Colorless crystal/acetone | 271.5–273.5 (decomp.) | 8 |
| 2-Hydroxy-5-nitroacetophenone + Dimethylformamide | 6-Nitro-4-oxo-4H-1-benzopyran-3-carboxaldehyde | Pale yellowish prisms/acetone | 163–164 | 9 |
| 2,4-Dihydroxyacetophenone + Dimethylformamide | 7-Hydroxy-4-oxo-4H-1-benzopyran-3-carboxaldehyde | Yellow prisms/Dimethylformamide acetone-water | 268–271 (decomp.) | 11 |
| 2-Hydroxy-4-methoxyacetophenone + Dimethylformamide | 7-Methoxy-4-oxo-4H-1-benzopyran-3-carboxaldehyde | Pale yellowish needles/acetone | 188–190 | 12 |

| Starting materials | Product | Crystal form/Recrystallization solvent | m.p. (°C) | Example No. |
|---|---|---|---|---|
| 2-Hydroxy-5-ethyl acetophenone + Dimethylformamide | 6-Ethyl-4-oxo-4H-1-benzopyran-3-carboxaldehyde | Colorless scales/ethyl acetate | 109–111 | 13 |
| 2-Hydroxy-5-n-butyl acetophenone + Dimethylformamide | 6-n-Butyl-4-oxo-4H-1-benzopyran-3-carboxaldehyde | Colorless needles/ligroin | 86.5–88 | 14 |
| 2-Hydroxy-5-methoxy acetophenone + Dimethylformamide | 6-Methoxy-4-oxo-4H-1-benzopyran-3-carboxaldehyde | Pale yellowish plate/acetone | 165–166 | 15 |
| 2-Hydroxy-5-acetamino acetophenone + Dimethylformamide | 6-Acetamino-4-oxo-4H-1-benzopyran-3-carboxaldehyde | Pale yellowish powder/acetone | 231–233 | 16 |
| 2-Hydroxy-5-n-butyl acetophenone + Dimethylformamide | 6-n-Butyl-4-oxo-4H-1-benzopyran-3-carboxaldehyde | Colorless needles/cyclohexane-ligroin | 86.5–88.5 | 17 |
| 2-Hydroxy-3,5-dimethyl acetophenone + Dimethylformamide | 6,8-Dimethyl-4-oxo-4H-1-benzopyran-3-carboxaldehyde | Colorless needles/DMF + acetone | 186–187 | 18 |
| 2-Hydroxy-3,5-dibromo acetophenone + Dimethylformamide | 6,8-Dibromo-4-oxo-4H-1-benzopyran-3-carboxaldehyde | Colorless needles/acetone | 177–178 | 19 |
| 2-Hydroxy-5-dimethylamino acetophenone + Dimethylformamide | 6-Dimethylamino-4-oxo-4H-1-benzopyran-3-carboxaldehyde | Colorless needles/DMF + acetone | 154–154.5 | 20 |
| 2-Hydroxy-5-isopropyl acetophenone + Dimethylformamide | 6-Isopropyl-4-oxo-4H-1-benzopyran-3-carboxaldehyde | Yellowish needles/ethyl acetate-petroleum ether | 98–99.5 | 21 |
| 2-Hydroxy-5-n-propyl acetophenone + Dimethylformamide | 6-n-Propyl-4-oxo-4H-1-benzopyran-3-carboxaldehyde | Pale yellowish scales/ligroin-ethyl acetate | 100–102 | 22 |
| 2-Hydroxy-6-methoxy-acetophenone + Dimethylformamide | 5-Methoxy-4-oxo-4H-1-benzopyran-3-carboxaldehyde | Pale yellow plates/acetone | 115–116 | 23 |

| Starting materials | Product | Crystal form/Recrystallization solvent | m.p. (°C) | Example No. |
|---|---|---|---|---|
| +<br>Dimethylformamide | | | | |

We claim:
1. 7-acetoxy-4-oxo-4H-1-benzoypyran-3-carboxaldehyde.
2. 6-methyl-4-oxo-4H-1-benzopyran-3-carboxaldehyde.
3. 6-chloro-4-oxo-4H-1-benzopyran-3-carboxaldehyde.
4. 6-carboxy-4-oxo-4H-1-benzopyran-3-carboxaldehyde.
5. 6-nitro-4-oxo-4H-1-benzopyran-3-carboxaldehyde.
6. 7-hydroxy-4-oxo-4H-1-benzopyran-3-carboxaldehyde.
7. 7-methoxy-4-oxo-4H-1-benzopyran-3-carboxaldehyde.
8. 6-n-butyl-4-oxo-4H-1-benzopyran-3-carboxaldehyde.
9. 6-methoxy-4-oxo-4H-1-benzopyran-3-carboxaldehyde.
10. 6-acetamino-4-oxo-4H-1-benzopyran-3-carboxaldehyde.
11. A compound which is 6,8-dimethyl-4-oxo-4H-1-benzopyran-3-carboxaldehyde.
12. A compound which is 6,8-dibromo-4-oxo-4H-1-benzopyran-3-carboxaldehyde.
13. 6-ethyl-4-oxo-4H-1-benzopyran-3-carboxaldehyde.
14. 6-dimethyl-amino-4-oxo-4H-1-benzopyran-3-carboxaldehyde.
15. 6-iso-propyl-4-oxo-4H-1-benzopyran-3-carboxaldehyde.
16. 5-acetoxy-4-oxo-4H-1-benzopyran-3-carboxaldehyde.
17. 6-n-propyl-4-oxo-4H-1-benzopyran-3-carboxaldehyde.
18. 5-methoxy-4-oxo-4H-1-benzopyran-3-carboxaldehyde.

* * * * *

UNITED STATES PATENT OFFICE
CERTIFICATE OF CORRECTION

Patent No. 3,984,441                    Dated October 5, 1976

Inventor(s) Akira Nohara et al.

It is certified that error appears in the above-identified patent and that said Letters Patent are hereby corrected as shown below:

Column 2, line 17: Change "alkylcrbonyloxy" to

--alkylcarbonyloxy--.

Column 3, line 4: Change "or" to --of--.

line 59: After "1" insert --to--;

Change "an" to --as--.

line 65: After "in" insert --a--.

Column 4, lines 7 and 8: Change "dibenzyl bromide" to

--benzyl bromide--.

lines 31 and 32: Change "$C_{18}H_{12}O_4$: Calcd. C, 73.97; H, 4.14 Found C, 73.88; H, 4.23" to --$C_{10}H_6O_3$: Calcd. C, 68.96; H, 3.47 Found C, 68.70; H, 3.37-- line 64: Change "benzpyran" to --benzopyran--.

UNITED STATES PATENT OFFICE
CERTIFICATE OF CORRECTION

Patent No. 3,984,441   Dated October 5, 1976

Inventor(s) Akira Nohara et al.

It is certified that error appears in the above-identified patent and that said Letters Patent are hereby corrected as shown below:

Column 6, Example No. 20, in the column marked "m.p.(°C)":

Change "154" to --153--.

Signed and Sealed this

Sixth Day of December 1977

[SEAL]

Attest:

RUTH C. MASON  
*Attesting Officer*

LUTRELLE F. PARKER  
*Acting Commissioner of Patents and Trademarks*